US009883787B2

(12) United States Patent
Kasumi et al.

(10) Patent No.: US 9,883,787 B2
(45) Date of Patent: Feb. 6, 2018

(54) MEDICAL APPARATUS SYSTEM

(71) Applicant: OLYMPUS CORPORATION, Hachioji-shi, Tokyo (JP)

(72) Inventors: Makoto Kasumi, Hachioji (JP); Hideki Tashiro, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/171,351

(22) Filed: Jun. 2, 2016

(65) Prior Publication Data

US 2016/0270629 A1 Sep. 22, 2016

Related U.S. Application Data

(63) Continuation of application No. PCT/JP2015/059655, filed on Mar. 27, 2015.

(30) Foreign Application Priority Data

Jun. 19, 2014 (JP) .................................. 2014-126597

(51) Int. Cl.
*A61B 1/00* (2006.01)
*H02J 7/04* (2006.01)
(Continued)

(52) U.S. Cl.
CPC ...... *A61B 1/00009* (2013.01); *A61B 1/00006* (2013.01); *A61B 1/00025* (2013.01);
(Continued)

(58) Field of Classification Search
CPC ............ A61B 1/00006; A61B 1/00034; A61B 1/00036; A61B 2017/00734;
(Continued)

(56) References Cited

U.S. PATENT DOCUMENTS 4,331,403 A * 5/1982 Ohno ..................... A61B 1/045
600/112
2006/0220613 A1* 10/2006 Abe .................... A61B 1/00034
320/114
(Continued)

FOREIGN PATENT DOCUMENTS

JP 2006-280542 A 10/2006
JP 2009-034416 A 2/2009
(Continued)

OTHER PUBLICATIONS

Feb. 9, 2016 Decision to Grant issued in Japanese Patent Application No. 2015-559761.
(Continued)

*Primary Examiner* — Timothy J Neal
*Assistant Examiner* — Aaron B Fairchild
(74) *Attorney, Agent, or Firm* — Oliff PLC

(57) ABSTRACT

A medical apparatus system includes a first communication section provided in a medical apparatus and configured to transmit battery use information including information concerning a residual capacity of a first battery, a charger including a power supply section configured to charge a second battery, and a control section configured to set a charging current of the power supply section on the basis of the battery use information and battery charging information including a residual capacity of the second battery such that a capacity insufficiency residual time, which is time until the residual capacity of the first battery changes to a state of residual capacity insufficiency, is equal to or longer than a charging completion residual time, which is time until the second battery changes to a completely charged state.

10 Claims, 7 Drawing Sheets

(51) Int. Cl.
| | |
|---|---|
| *H01M 10/44* | (2006.01) |
| *A61B 1/04* | (2006.01) |
| *H01M 10/48* | (2006.01) |
| *H02J 7/00* | (2006.01) |
| *H02J 7/02* | (2016.01) |
| *H01M 10/42* | (2006.01) |

(52) U.S. Cl.
CPC ...... *A61B 1/00027* (2013.01); *A61B 1/00034* (2013.01); *A61B 1/00036* (2013.01); *A61B 1/04* (2013.01); *H01M 10/425* (2013.01); *H01M 10/44* (2013.01); *H01M 10/48* (2013.01); *H02J 7/00* (2013.01); *H02J 7/007* (2013.01); *H02J 7/0044* (2013.01); *H02J 7/0068* (2013.01); *H02J 7/02* (2013.01); *A61B 2560/0204* (2013.01); *A61B 2560/0214* (2013.01); *H01M 2010/4271* (2013.01); *H01M 2010/4278* (2013.01)

(58) Field of Classification Search
CPC ........ A61B 2560/0214; A61B 1/00025; A61B 1/00027; A61B 1/00032; A61B 2560/0204; H02J 7/044; H01M 10/44

USPC ........................................................ 600/132
See application file for complete search history.

(56) References Cited

U.S. PATENT DOCUMENTS

2006/0220614 A1   10/2006  Abe
2015/0318726 A1*  11/2015  Luo ..................... H01M 10/441
                                                      320/134

FOREIGN PATENT DOCUMENTS

| JP | 5362930 B1 * | 12/2013 | ............ H01M 10/44 |
| JP | 2014-096940 A | 5/2014 | |
| JP | 2015-015827 A | 1/2015 | |
| WO | 2014/073475 A1 | 5/2014 | |
| WO | 2015/001930 A1 | 1/2015 | |

OTHER PUBLICATIONS

Jun. 9, 2015 Search Report issued in International Patent Application No. PCT/JP2015/059655.

\* cited by examiner

MEDICAL APPARATUS SYSTEM

CROSS REFERENCE TO RELATED APPLICATION

This application is a continuation application of PCT/JP2015/059655 filed on Mar. 27, 2015 and claims benefit of Japanese Application No. 2014-126597 filed in Japan on Jun. 19, 2014, the entire contents of which are incorporated herein by this reference.

BACKGROUND OF THE INVENTION

1. Field of the Invention

The present invention relates to a medical apparatus system that performs charging management of a battery mounted on an apparatus.

2. Description of the Related Art

According to progress of a semiconductor technique, various apparatuses such as a cellular phone, a smartphone, and a tablet PC have been reduced in size and reduced in power consumption and have been configured to be portable. A portable apparatus is often mounted with a battery and configured to be continuously usable by charging the battery.

In a medical field as well, a reduction in size of an apparatus has been facilitated. For example, as an endoscope having relatively large power consumption, a portable endoscope mounted with a rechargeable battery has been developed. Endoscope apparatuses are used in various fields such as a medical field and an industrial field. The endoscope apparatus in the medical field is used for an observation of an organ in a body cavity, curative treatment performed using a treatment instrument, a surgical operation under an endoscopic observation, and the like. Note that a battery-driven electronic endoscope is disclosed in Japanese Patent Application Laid-Open Publication No. 2006-280542.

The endoscope apparatus includes a processor that processes a picked-up image obtained by an electronic endoscope. Display on a monitor and recording in a recording medium of a medical image are performed by the processor. The portable endoscope incorporates a radio communication section that transmits an endoscopic image obtained by an image pickup device to the processor, a light source device for illuminating an object, and the like and is wirelessly configured. Therefore, the portable endoscope is excellent in portability and workability.

However, when the portability is taken into account, weight of a battery mounted on the electronic endoscope is limited. A battery capacity is also limited. Therefore, the electronic endoscope cannot always be driven by only one battery mounted on the electronic endoscope in an entire period of manipulation performed using the endoscope. Therefore, it is necessary to take into account replacement of the battery halfway in the manipulation. Even in this case, no problem arises if many batteries are stored as spares. However, realistically, a method of preparing several batteries and, while charging a battery not in use, when a residual capacity of a battery in use becomes insufficient, replacing the battery in use with the charged battery is adopted.

Note that a charger for charging the battery is configured to charge the battery with a current amount determined in advance. However, some chargers can change a charging current according to setting by a user. It is possible to perform quick charging by setting the charging current to a large current. It is also possible to change the battery to a completely charged state in a relatively short time.

SUMMARY OF THE INVENTION

A medical apparatus system according to an aspect of the present invention includes: a medical apparatus driven by a first battery; a first communication section provided in the medical apparatus and configured to transmit battery use information including information concerning a residual capacity of the first battery; a charger including a power supply section configured to charge a second battery, which is a charging target; a second communication section provided in the charger and configured to communicate with the first communication section and acquire the battery use information; and a control section configured to set a charging current of the power supply section on the basis of the battery use information acquired by the second communication section and battery charging information including a residual capacity of the second battery included in the charger such that a capacity insufficiency residual time, which is time until the residual capacity of the first battery changes to a state of residual capacity insufficiency, is equal to or longer than a charging completion residual time, which is time until the second battery changes to a completely charged state.

A medical apparatus system according to another aspect of the present invention includes: a medical apparatus driven by a first battery; a first communication section provided in the medical apparatus and configured to transmit battery use information including information concerning a residual capacity of the first battery; a charger including a power supply section configured to charge a second battery, which is a charging target; a second communication section provided in the charger and configured to transmit battery charging information including a residual capacity of the second battery; a third communication section configured to communicate with the first communication section and the second communication section and acquire the battery use information and the battery charging information; and a control section configured to set a charging current of the power supply section on the basis of the battery use information and the battery charging information acquired by the third communication section such that a capacity insufficiency residual time, which is time until the residual capacity of the first battery changes to a state of residual capacity insufficiency, is equal to or longer than a charging completion residual time, which is time until the second battery changes to a completely charged state.

DETAILED DESCRIPTION OF THE PREFERRED EMBODIMENTS

Embodiments of the present invention are explained in detail below with reference to the drawings.
(First Embodiment)

Figure 1A:
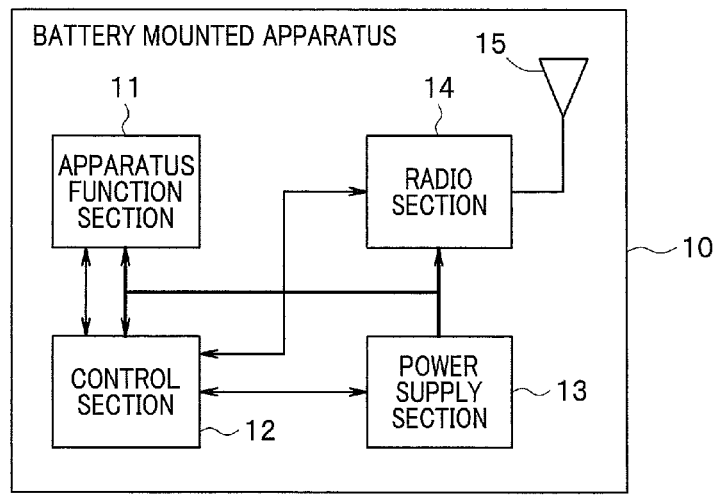
FIG. 1A is a block diagram showing a battery management system according to a first embodiment of the present invention.
Figure 1B:
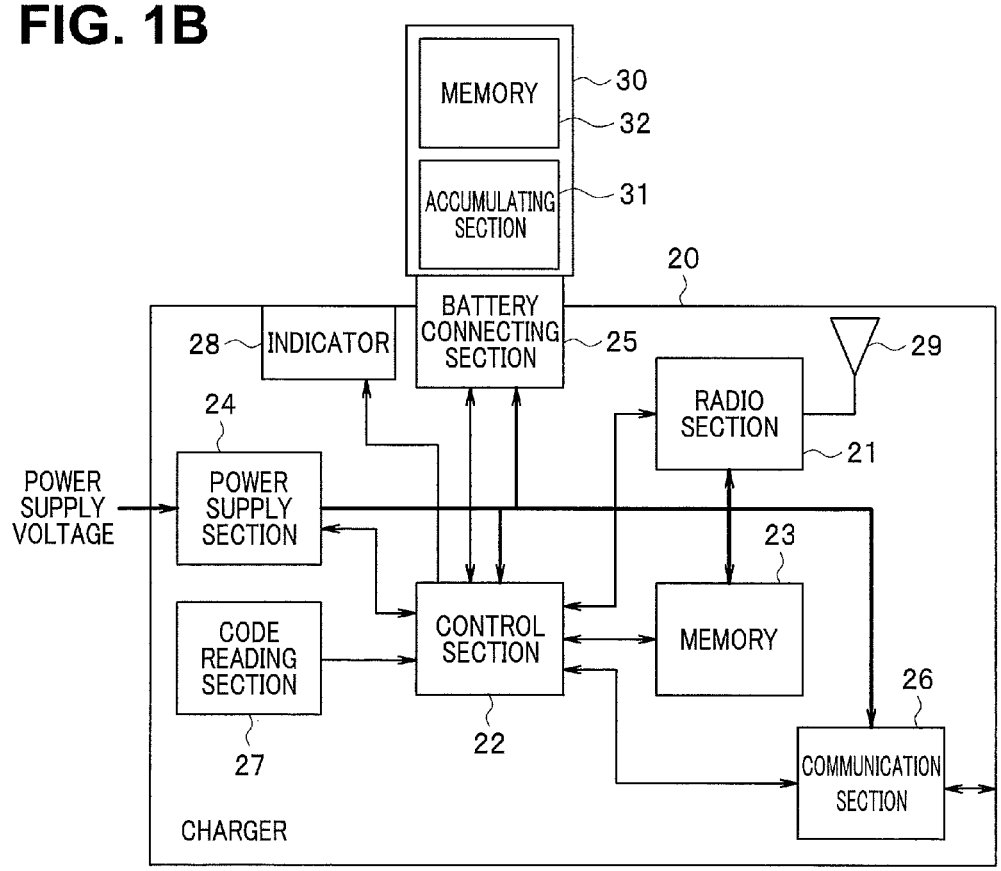
FIG. 1B is a block diagram showing the battery management system according to the first embodiment of the present invention.

FIG. 1A and FIG. 1B are each a block diagram showing a battery management system according to a first embodiment of the present invention. FIG. 1A shows a configuration of a battery mounted apparatus 10 and FIG. 1B shows a configuration of a charger 20.

The battery mounted apparatus 10 is configured by an apparatus function section 11, a control section 12, a power supply section 13, and a radio section 14. The apparatus function section 11 is a portion that realizes predetermined functions of the battery mounted apparatus 10. For example, when the battery mounted apparatus 10 is a smartphone, the apparatus function section 11 is configured by respective circuit sections that realize functions of the smartphone, for example, circuits that realize a telephone function, a packet communication function, a packet processing function, a display function, a sound function, and the like. For example, when the battery mounted apparatus 10 is a portable endoscope, the apparatus function section 11 is configured by circuits such as an image pickup section, a light source section, and an image processing section.

The power supply section 13 is configured to be capable of supplying electric power to the apparatus function section 11, the control section 12, and the radio section 14. Note that thick lines in FIG. 1A and FIG. 1B indicate power supply lines. In the present embodiment, in the power supply section 13, a not-shown rechargeable and detachable battery is adopted. The power supply section 13 is configured to generate a predetermined power supply voltage using an output of the battery (hereinafter referred to as battery in use) and supply the power supply voltage to the respective sections.

The control section 12 controls the respective sections of the battery mounted apparatus 10. The control section 12 controls the apparatus function section 11 to realize functions of the apparatus and controls the power supply section 13 to supply electric power to the respective sections. Further, in the present embodiment, the control section 12 is configured to acquire information concerning the battery in use from the power supply section 13. For example, the control section 12 acquires information concerning a battery capacity (a rated capacity) in a completely charged state and a present residual capacity of the battery in use (hereinafter referred to as battery use information). Note that the battery use information concerning the residual capacity can be acquired by measuring a discharge voltage or current of the battery in use. Concerning the battery residual capacity, the control section 12 is configured to acquire information at a predetermined time interval.

The control section 12 outputs the acquired battery use information to the radio section 14. The radio section 14 is controlled by the control section 12 to be capable of transmitting the battery use information by radio at a predetermined time interval via an antenna 15. Note that, when a radio function is provided in the apparatus function section 11, the radio section 14 may transmit the battery use information using the radio function in the apparatus function section 11.

The charger 20 includes a radio section 21 functioning as an acquiring section as well. The radio section 21 is capable of performing communication with the radio section 14 in the battery mounted apparatus 10 by radio via an antenna 29. The radio section 21 is configured to receive the battery use information from the radio section 14 and give the battery use information to the control section 22. Note that the radio sections 14 and 21 are explained as transmitting and receiving the battery use information by radio communication. However, a wired communication section capable of performed wired communication may be provided instead of the radio sections 14 and 21 to transmit the battery use information by wired communication. The control section 22 is configured to be capable of giving the received battery use information to a memory 23 and causing the memory 23 to store the battery use information.

The charger 20 includes a battery connecting section 25 functioning as an acquiring section as well. A plurality of batteries of a type same as a type of the battery in use can be respectively detachably connected to the battery connecting section 25 as a charging target battery 30. The charger 20 includes a power supply section 24 in order to charge the charging target battery 30. A power supply voltage is supplied to the power supply section 24 from a not-shown commercial AC power supply or AC adapter. The power supply section 24 is configured to DC/DC-convert the supplied power supply voltage to generate predetermined electric power and supply the predetermined electric power to the radio section 21, the control section 22, the memory 23, the battery connecting section 25, and a communication section 26.

In the present embodiment, the power supply section 24 is controlled by the control section 22 to be capable of changing electric power supplied to the battery connecting section 25. That is, the power supply section 24 is configured to be capable of changing an electric current supplied to the battery connecting section 25 and charge the charging target battery 30 with different charging currents.

In order to control a charging current of the charging target battery 30, the control section 22 acquires information concerning a battery capacity (a rated capacity) in a completely charged state and a present capacity (hereinafter referred to as charging capacity) of the charging target battery 30 (hereinafter referred to as battery charging information). Note that the battery charging information concerning the charging capacity can be acquired by measuring a discharge voltage or current of the charging target battery 30. The charging target battery 30 is mounted on the battery connecting section 25, whereby the control section 22 can acquire the battery charging information. Concerning the charging capacity, the control section 22 is configured to acquire information at a predetermined time interval.

That is, in the present embodiment, the control section 22 acquires the battery use information including the information concerning the residual capacity of the battery in use used in the battery mounted apparatus 10 and the battery charging information including the information concerning the charging capacity of the charging target battery 30 charged by the charger 20. The control section 22 estimates, on the basis of the battery use information or a history of the battery use information, a residual time, which is time until the residual capacity of the battery in use used in the battery mounted apparatus 10 changes to a state of residual capacity insufficiency in which the residual capacity is insufficient for causing the battery mounted apparatus 10 to operate (hereinafter referred to as capacity insufficiency residual time). The control section 22 calculates, on the basis of the battery charging information, a residual time, which is time until the charging target battery 30 being charged in the charger 20 changes to the completely charged state (hereinafter referred to as charging completion residual time).

In the present embodiment, the control section 22 is configured to change the charging current of the power supply section 24 such that the charging of the charging target battery 30 is completed within the capacity insufficiency residual time, that is, the capacity insufficiency residual time is equal to or longer than the charging completion residual time. Note that, in order to accurately calculate the charging completion residual time, the control section 22 is configured to measure an ambient temperature as well with a not-shown thermometer.

The charger 20 can charge batteries of a type same as a type of the battery in use while replacing the batteries. The control section 22 is configured to acquire identification information of the charging target battery 30 in order to individually manage the charging target battery 30 connected to the battery connecting section 25. In an example shown in FIG. 1B, the charging target battery 30 is configured by an accumulating section 31 and a memory 32 configuring a secondary battery. Identification information of the charging target battery 30 is stored in the memory 32. In this case, the charging target battery 30 is mounted on the battery connecting section 25, whereby the control section 22 is capable of reading out the identification information from the memory 32 and recognizing the charging target battery 30.

A battery not including a memory is sometimes mounted on the battery connecting section 25 as the charging target battery 30. In this case, a code reading section 27 reads out information such as a barcode provided in the battery and gives the information to the control section 22, whereby the control section 22 is capable of recognizing the battery mounted on the battery connecting section 25. Note that the control section 22 may be capable of acquiring identification information concerning the battery using not only the memory and the barcode but also an IC tag, an RFID, and the like.

The control section 22 is configured to give, for each of respective batteries, information such as a history concerning charging to the memory 23 and cause the memory 23 to store the information. In the memory 23, identification information, a history concerning charging, and the like are stored for each of a plurality of batteries chargeable in the charger 20 including the charging target battery 30. Consequently, the control section 22 is capable of performing control for, for example, prohibiting charging of a battery that has reached an upper limit of the number of times of charging.

An indicator 28 is provided in the charger 20. Information concerning a charging state of the charging target battery 30 is given to the indicator 28 from the control section 22. The indicator 28 is configured to be capable of displaying the information. For example, the control section 22 can cause the indicator 28 to display, for example, time when charging is completed. The communication section 26 is provided in the charger 20. The communication section 26 is controlled by the control section 22 to be capable of transmitting and receiving information concerning the charging target battery 30 to and from not-shown other apparatuses (not shown in the figure).

Figure 2:
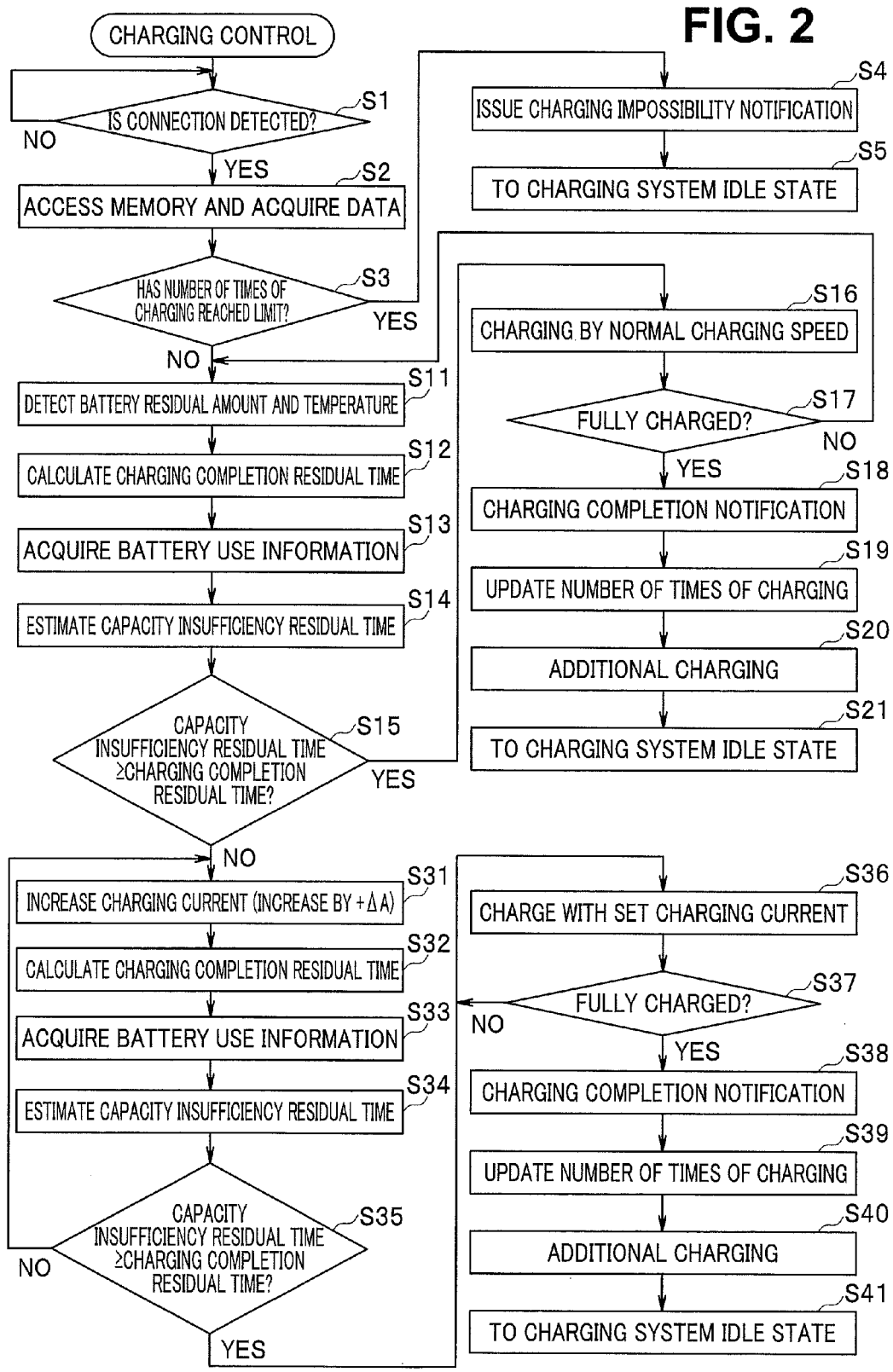
FIG. 2 is a flowchart for explaining an operation of the first embodiment.

An operation of the embodiment configured as explained above is explained with reference to FIG. 2 to FIG. 4. FIG. 2 is a flowchart for explaining the operation of the first embodiment.

It is assumed that a not-shown battery in use is mounted on the power supply section 13 of the battery mounted apparatus 10. The apparatus function section 11 receives electric power from the power supply section 13 and operates. The control section 12 acquires battery use information including information concerning a present residual capacity of the battery in use from the power supply section 13 at a predetermined time interval. The control section 12 transmits the acquired battery use information to the charger 20 via the radio section 14. The control section 12 causes the radio section 14 to repeatedly transmit the battery use information at a predetermined time interval.

In step S1 in FIG. 2, the charger 20 determines whether the charging target battery 30 is connected to the battery connecting section 25. When the user connects a predetermined battery to the battery connecting section 25, the control section 22 determines that the charging target battery 30 is connected to the battery connecting section 25 and shifts processing to step S2.

In step S2, the control section 22 reads out information stored in the memory 32 of the charging target battery 30 via the battery connecting section 25. Note that, when a battery to be charged does not include a memory, information concerning the battery mounted on the code reading section 27 can be given to the control section 22 by another method, for example, by the user mounting the battery on the battery connecting section 25 after holding a printed barcode of the battery over the code reading section 27.

The control section 22 reads out the information concerning the charging target battery 30 stored in the memory 23 on the basis of the read out information concerning the battery and determines whether the number of times of charging of the charging target battery 30 has reached a specified number of times determined in advance (step S3). When the number of times of charging has reached the specified number of times, the control section 22 determines that charging of the battery 30 is impossible, issues a charging impossibility notification and outputs the charging impossibility notification to the indicator 28 (step S4), and shifts to a charging system idle state (step S5). Consequently, the indicator 28 can indicate that the charging of the battery 30 is impossible and cause the user to recognize that the charging target battery 30 cannot be charged.

When the number of times of charging has not reached the specified number of times, in order to determine a charging current, the control section 22 shifts the processing to step S11, acquires the battery charging information including the information concerning the charging capacity from the charging target battery 30, and acquires information concerning an ambient temperature. The control section 22 calculates, on the basis of the rated capacity, the present charging capacity, and the ambient temperature of charging target battery 30, a charging completion residual time, which is time until the charging target battery 30 changes to the completely charged state when the charging target battery 30 is charged with a normal charging current (step S12).

In the next step S13, the control section 22 acquires battery use information of the battery in use mounted on the battery mounted apparatus 10. The control section 22 estimates, on the basis of a minimum residual capacity sufficient for causing the battery mounted apparatus 10 to operate, a present residual capacity of the battery in use, or a history of the battery in use, a capacity insufficiency residual time, which is time until the battery in use changes to a state of residual capacity insufficiency (step S14).

In step S15, the control section 22 determines whether the capacity insufficiency residual time is equal to or longer than the charging completion residual time calculated in step S12. In the case of YES determination, the control section 22 shifts the processing to step S16 and controls the power supply section 24 such that charging by the normal charging current is performed. Consequently, the power supply section 24 charges the charging target battery 30 via the battery connecting section 25 with the normal charging current.

In step S17, the control section 22 determines whether a charging capacity has reached the rated capacity, that is, whether the charging target battery 30 is fully charged. Note that, although not clearly described in FIG. 2, the determination in step S17 is performed at a predetermined time interval. When determining that the charging target battery 30 is fully charged, in step S18, the control section 22 causes the indicator 28 to display a notification of charging completion. Subsequently, the control section 22 updates the information concerning the number of times of charging of the charging target battery 30 stored in the memory 23 (step S19). The control section 22 instructs, taking into account electric discharge until the charging target battery 30 is replaced with the battery in use, the power supply section 24 to perform additional charging (step S20) and shifts to the charging system idle state (step S21).

When determining in step S17 that the charging target battery 30 has not reached full charge, the control section 22 returns the processing to step S11 and acquires a charging capacity and an ambient temperature of the charging target battery 30. In step S12, the control section 22 calculates a charging completion residual time at the time when the charging target battery 30 is charged with the normal charging current. In step S13, the control section 22 acquires battery use information of the battery in use again and estimates a capacity insufficiency residual time (step S14).

In step S15, the control section 22 determines whether the capacity insufficiency residual time is equal to or longer than the charging completion residual time calculated in step S12. In the case of YES determination, the control section 22 shifts the processing to step S16 and repeats the processing in steps S11 to S17 until the charging target battery 30 is fully charged.

In this way, even when the charging insufficiency residual time is equal to or longer than the charging completion residual time calculated in step S12, that is, even when the charging target battery 30 is charged with the normal charging current, when the charging is completed before the capacity insufficiency residual time elapses, the control section 22 instructs the power supply section 24 to perform charging with the normal charging current. Consequently, it is possible to complete, without adversely affecting life of the charging target battery 30, the charging of the charging target battery 30 before the capacity of the battery in use becomes insufficient.

It is assumed that it is determined NO in first determination or subsequent determination because, for example, power consumption of the apparatus function section 11 increases or the residual capacity of the battery in use decreases from the beginning. In this case, the control section 22 determines that, when the charging is continued with the normal charging current, the charging target battery 30 cannot be fully charged before the residual capacity of the battery in use becomes insufficient, shifts the processing to step S31, and performs quick charging.

In an example shown in FIG. 2, setting of a charging amount of the quick charging is changed stepwise to calculate a charging current to prevent the charging current from increasing more than necessary. That is, in step S31, the control section 22 performs setting for increasing the charging current. For example, the control section 22 performs setting for increasing the charging current by $+\Delta A$ with respect to a present charging current. Subsequently, the control section 22 calculates a charging completion residual time at the time when the charging target battery 30 is charged with the charging current set anew.

In the next step S33, the control section 22 acquires battery use information of the battery in use. In step S34, the control section 22 estimates a capacity insufficiency residual time. In step S35, the control section 22 determines whether the capacity insufficiency residual time is equal to or longer than the charging completion residual time calculated in step S32.

When determining in step S35 that the charging completion residual time is longer than the capacity insufficiency residual time, the control section 22 returns the processing to step S31 and performs setting for further increasing the charging current by $+\Delta A$. In steps S32 to S34, the control section 22 performs calculation of a charging completion residual time at the time when the charging target battery 30 is charged with the charging current set anew and estimation of a capacity insufficiency residual time based on the battery use information. In step S35, the control section 22 determines again whether the capacity insufficiency residual time is equal to or longer than the charging completion residual time calculated in step S32. Thereafter, the processing in steps S31 to S35 is repeated. When determining that the capacity insufficiency residual time is equal to or longer than the charging completion residual time calculated in step S32, the control section 22 shifts the processing to step S36.

The power supply section 24 charges the charging target battery 30 with the set charging current. In step S37, the control section 22 determines whether the charging target battery 30 is fully charged and causes the power supply section 24 to continue the charging with the set charging current until the charging target battery 30 is fully charged. Note that the processing in step S37 is performed at a predetermined time interval.

When determining in step S37 that the charging target battery 30 is fully charged, in step S38, the control section 22 causes the indicator 28 to display a notification of charging completion. Subsequently, the control section 22 updates the information concerning the number of times of charging of the charging target battery 30 stored in the memory 23 (step S39). The control section 22 instructs, taking into account electric discharge until the charging target battery 30 is replaced with the battery in use, the power supply section 24 to perform additional charging (step S40) and shifts to the charging system idle state (step S41).

In steps S31 to S41, while acquiring the battery use information of the battery in use at the predetermined time interval and estimating the capacity insufficiency residual time, the control section 22 controls the charging current and performs the charging such that the charging completion residual time decreases to time equal to or shorter than the capacity insufficiency residual time. Consequently, it is possible to surely fully charge the charging target battery before the residual capacity of the battery in use becomes insufficient. Charging with a necessary minimum charging current is enabled to prevent battery life from decreasing.

Figure 3:
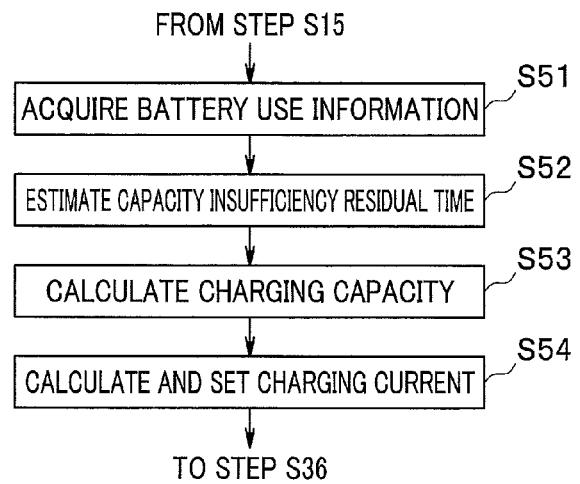
FIG. 3 is a flowchart showing a flow executed instead of steps S31 to S35 in FIG. 2.
Figure 4:
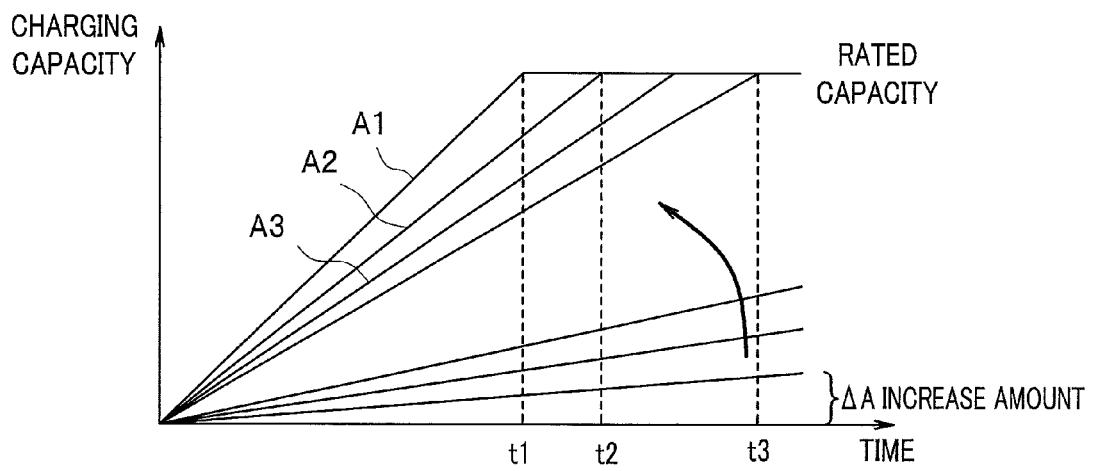
FIG. 4 is a graph for explaining charging in FIG. 3 with time plotted on a horizontal axis and a charging capacity plotted on a vertical axis.

Note that, in FIG. 2, an example is shown in which the setting of the charging current is increased stepwise in steps S31 to S35. However, the setting of the charging current may be increased at a time to a charging current that should be set. FIG. 3 is a flowchart showing a flow executed instead of steps S31 to S35 in FIG. 2 in this case. FIG. 4 is a graph for explaining charging in FIG. 3 with time plotted on a horizontal axis and a charging capacity plotted on a vertical axis.

In step S51 in FIG. 3, the control section 22 acquires battery use information of the battery in use. Subsequently, the control section 22 estimates a capacity insufficiency residual time on the basis of the battery use information (step S52). Subsequently, in step S53, the control section 22 acquires information concerning a charging capacity of the charging target battery 30. In step S54, the control section 22 calculates and sets a charging current according to an arithmetic operation based on the capacity insufficiency residual time and the charging capacity.

FIG. 4 indicates that, when the charging current is changed, time required for charging completion of the charging target battery 30 changes. For example, a characteristic A in FIG. 4 indicates a change in the charging capacity at the time when the charging target battery 30 is charged with a maximum charging current and indicates that the charging target battery 30 is charged to a rated capacity at time t1. A characteristic A2 indicates that a charging current is smaller than the charging current of the characteristic A1. A characteristic A3 indicates that a charging current is smaller than the charging current of the characteristic A2. The characteristic A2 and the characteristic A3 respectively indicate that the charging target battery 30 is charged to the rated capacity at time t2 and time t3. As the charging current is larger, an increase in the charging capacity per unit time is larger. Respective straight lines in FIG. 3 indicate characteristics at the time when the charging current is increased by ΔA at a time in a direction indicated by an arrow and indicate a change in an increase amount per unit time of the charging capacity by increasing the charging current by ΔA at a time.

If a difference between the present charging capacity and the rated capacity of the charging target battery 30 and a capacity insufficiency residual time are known, it is possible to calculate to which inclination, that is, charging current the characteristics shown in FIG. 3 should be set to enable full charge within the capacity insufficiency residual time. In this way, the control section 22 is capable of calculating, at a time, a charging current that should be set. For example, the characteristics shown in FIG. 4 are described in a table and stored in the memory 23. Information is read out from the memory 23 on the basis of identification information of the charging target battery 30. Consequently, it is possible to easily calculate the charging current that should be set.

Note that, in the example shown in FIG. 2, when determining in step S37 that the charging target battery 30 is not fully charged, the control section 22 returns the processing to step S36. However, every time the determination processing in step S37 is executed a plurality of times or at every predetermined time interval, the control section 22 may return the processing to step S11 when the charging target battery 30 is not fully charged.

In this way, in the present embodiment, the control section 22 acquires the battery use information of the battery in use used in the battery mounted apparatus, estimates the capacity insufficiency residual time of the battery in use, and controls the charging current such that the charging of the charging target battery is completed in time shorter than the capacity insufficiency residual time. Consequently, it is possible to surely complete the charging before the capacity insufficiency residual time while preventing the charging current from unnecessarily increasing. Since the increase in the charging current is suppressed, it is possible to prevent life of the battery from decreasing. Since the battery in use can be replaced with a fully-charged battery before the residual capacity of the battery in use becomes insufficient, it is possible to continuously use the battery mounted apparatus.

(Second Embodiment)

Figure 5:
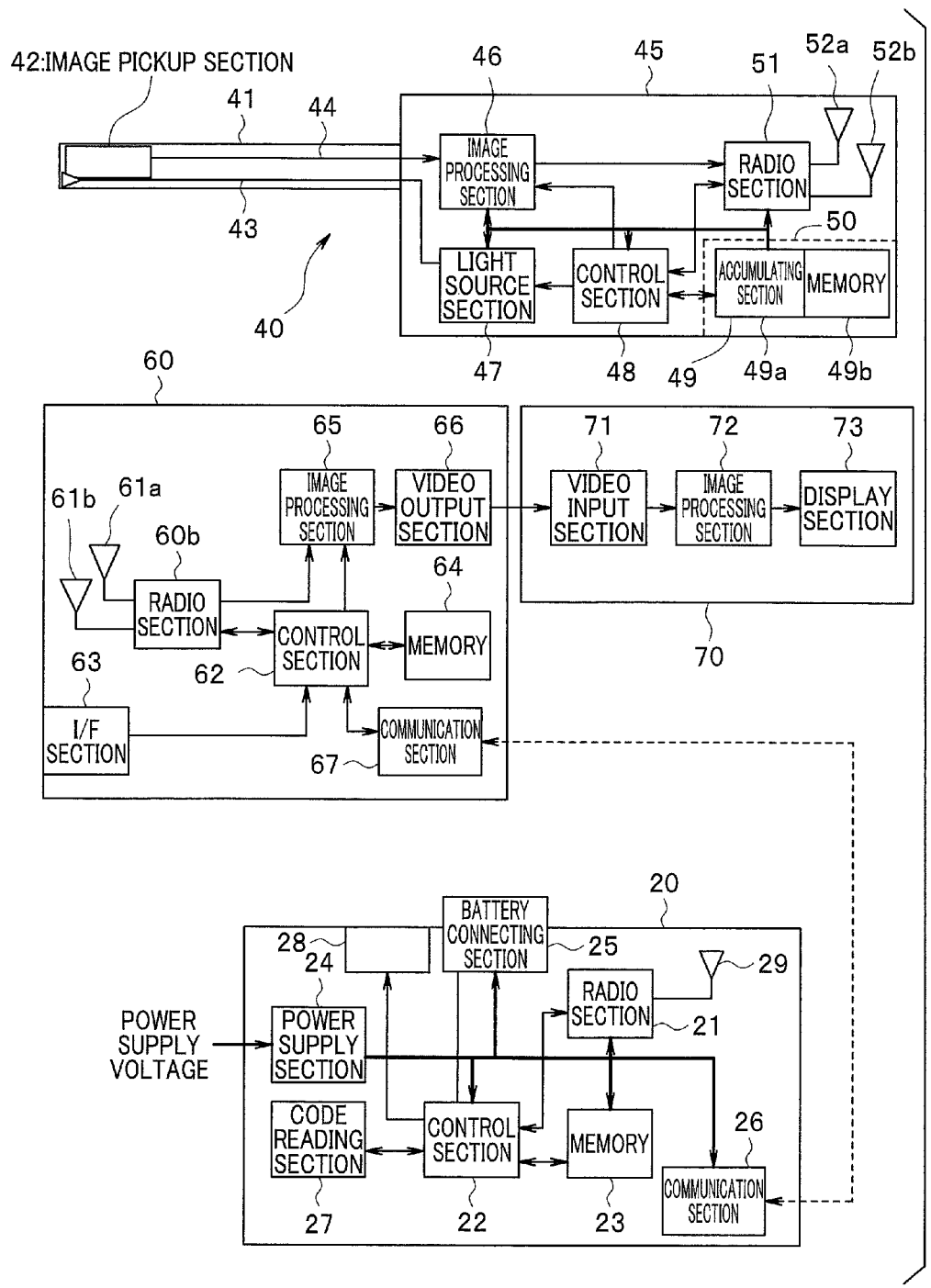
FIG. 5 is a block diagram showing a second embodiment of the present invention.
Figure 6:
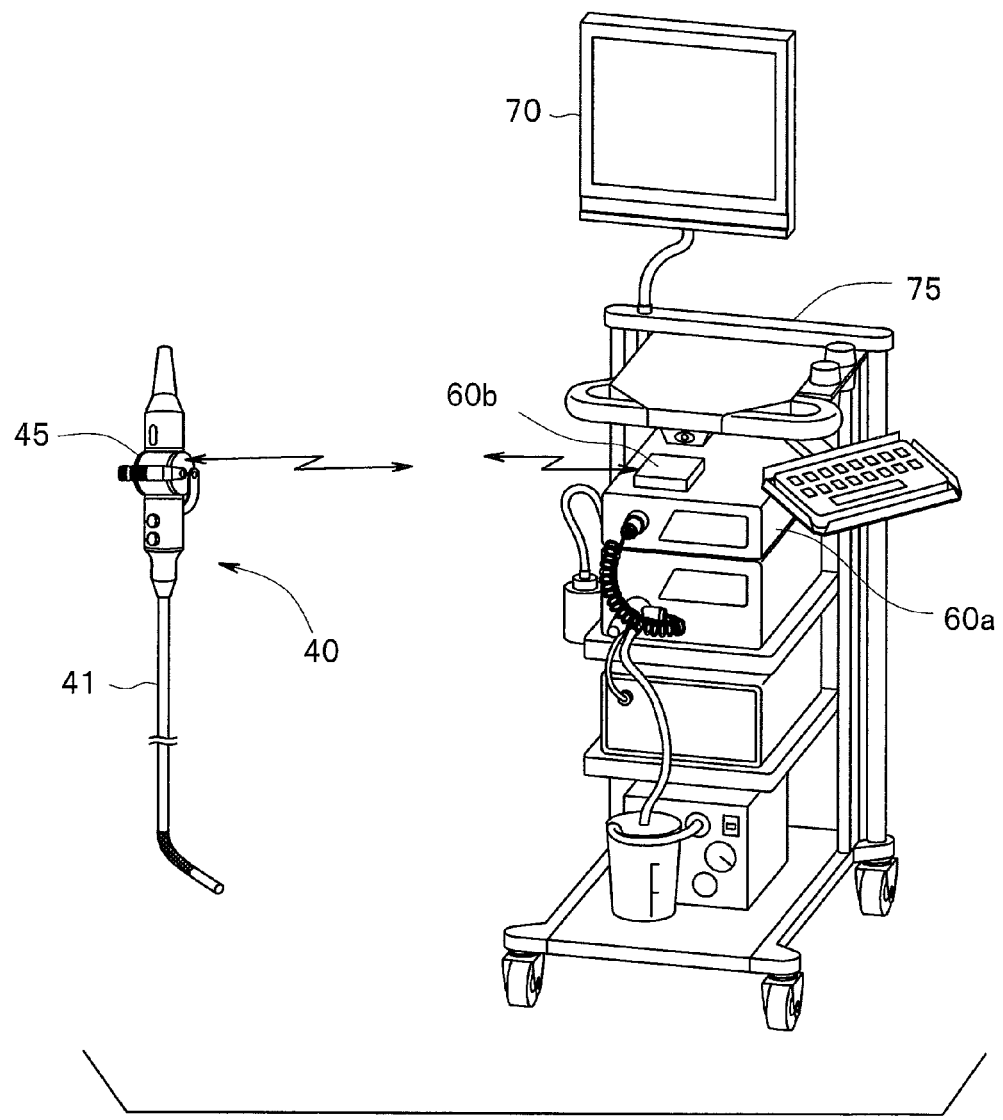
FIG. 6 is an explanatory diagram showing an overall configuration of an endoscope system disposed in an operating room.

FIG. 5 is a block diagram showing a second embodiment of the present invention. The present embodiment indicates an example in which a battery management system is applied to an endoscope system. In FIG. 5, components same as the components shown in FIG. 1A and FIG. 1B are denoted by the same reference numerals and signs and explanation of the components is omitted. In the present embodiment, the processing for determining a charging capacity of a battery executed in the control section of the charger in the first embodiment is executed in a control section of a processor. FIG. 6 is an explanatory diagram showing an overall configuration of an endoscope system disposed in an operating room.

As shown in FIG. 5, the endoscope system is configured by an endoscope 40, a processor 60, a monitor 70, and the charger 20. As shown in FIG. 6, in the operating room, various medical apparatuses and the monitor 70 are disposed on a cart 76. An example shown in FIG. 6 indicates an example in which a radio section 60b in the processor 60 shown in FIG. 5 is separately configured. A processor 60a, from which the radio section 60b is separately configured, is placed on the cart 76. The radio section 60b is connected to the processor 60a by a not-shown connector. Note that, as the medical apparatuses, for example, apparatuses such as an electric knife apparatus, a pneumoperitoneum apparatus, and a video recorder and a gas cylinder filled with carbon dioxide are also placed on the cart 76.

The endoscope 40 equivalent to the battery mounted apparatus 10 shown in FIG. 1A and FIG. 1B is mounted with a battery 49 and is wirelessly configured to be connected to the processor 60 by radio. The endoscope 40 includes an insertion section 41 on a distal end side and includes an operation section 45 on a proximal end side. An image pickup section 42 including an image pickup device configured by a CCD or CMOS sensor or the like is disposed at a distal end portion of the insertion section 41. A light source section 47 for illuminating an inside of a body cavity is provided in the operation section 45. The light source section 47 is controlled by a control section 48 to generate illumination light. The illumination light is guided to a distal end of the insertion section 41 by a light guide 43 and radiated on an object via a lens. Return light from the object forms an image on an image pickup surface of the image pickup section 42. The image pickup section 42 obtains a picked-up image based on an object optical image through photoelectric conversion. The image pickup section 42 supplies the picked-up image to an image processing section 46 via a signal line 44.

The battery 49 can be mounted on a power supply section 50 of the operation section 45. The power supply section 50 is configured to be capable of supplying electric power to the image processing section 46, the light source section 47, the control section 48, a radio section 51, and the image pickup section 42. Note that a thick line in FIG. 5 indicates a power supply line. In the power supply section 50, a rechargeable and detachable battery is mounted as the battery in use 49.

The power supply section 50 is configured to generate a predetermined power supply voltage using an output of the battery in use 49 and supplies the predetermined power supply voltage to the respective sections.

The control section 48 controls the respective sections of the endoscope 40. The image processing section 46 is controlled by the control section 48 to apply predetermined image processing to the picked-up image supplied from the image pickup section 42 and thereafter outputs the picked-up image to the radio section 51. The control section 48 controls the power supply section 50 to supply electric power to the respective sections. Further, the control section 48 acquires information concerning the battery in use 49 from the power supply section 50. The control section 48 acquires information concerning a rated capacity and a present residual capacity of the battery in use 49 (battery use information). Concerning a battery residual capacity, the control section 48 acquires information at a predetermined time interval. Note that the battery in use 49 is configured by an accumulating section 49a and a memory 49b configuring a secondary battery. Identification information is stored in the memory 49b.

The control section 48 outputs the acquired battery use information to the radio section 51. The radio section 51 is capable of performing, for example, radio communication by a 60 GHz band and radio communication by a 5 GHz band. The radio section 51 is controlled by the control section 48 to, for example, perform, concerning an image signal from the image processing section 46, the radio communication using the 60 GHz band and perform, concerning the battery use information, the radio communication using the 5 GHz. The radio section 51 is controlled by the control section 48 to sequentially transmit image signals obtained by image pickup via an antenna 52a by radio and transmits the battery use information via an antenna 52b at a predetermined time interval.

The radio section 60b is provided in the processor 60 shown in FIG. 5. The radio section 60b is capable of performing radio communication by the 60 GHz band and the 5 GHz band with the radio section 51 of the endoscope 40 and capable of performing radio communication by the 5 GHz band with the radio section 21 of the charger 20. The radio section 60b receives an image signal transmitted in the 60 GHz band via an antenna 61a. The radio section 60b receives, via an antenna 61b, the battery use information from the endoscope 40 and the battery charging information concerning the charging target battery from the charger 20 transmitted in the 5 GHz band. Note that the radio section 60b is configured to receive the battery use information and the battery charging information at a predetermined time interval.

The radio section 60b gives the received picked-up image to an image processing section 65 and gives the battery use information and the battery charging information to the control section 62. The control section 62 is configured to be capable of giving the received battery use information and battery charging information to a memory 64 and causing the memory 64 to store the battery use information and the battery charging information.

The image processing section 65 is controlled by the control section 62 to apply predetermined image processing to the inputted picked-up image and thereafter output the picked-up image to a video output section 66. The video output section 66 converts the inputted picked-up image into a format displayable on the monitor 70 and outputs the picked-up image to the monitor 70. A video input section 71 of the monitor 70 captures the picked-up image from the video output section 66 and outputs the picked-up image to an image processing section 72. The image processing section 72 applies predetermined display image processing to the inputted picked-up image and thereafter outputs the picked-up image to a display section 73. In this way, the picked-up image picked up by the image pickup section 42 is displayed on the display section 73 as a movie or a still image.

An I/F section 63 is an interface that receives user operation. For example, the I/F section 63 is configured by a front panel, various buttons of a control system, and the like. The I/F section 63 outputs an operation signal based on user operation to the control section 62. Various kinds of user operation such as designation of an observation mode of the endoscope 40 and setting concerning image display can be received by the I/F section 63. The control section 62 is capable of, for example, giving various instructions to the control section 48 of the endoscope 40 via the radio sections 60b and 51 on the basis of an operation signal from the I/F section 63.

In the present embodiment, in order to control the charging current of the power supply section 24 in the charger 20, the control section 62 acquires, at a predetermined time interval, the battery use information concerning the battery in use 49 or a history of the battery use information read out from the memory 64 and the battery charging information concerning the charging target battery 30. The control section 62 estimates, on the basis of the battery use information or the history, a capacity insufficiency residual time, which is time until a residual capacity of the battery in use 49 used in the endoscope 40 changes to a state of residual capacity insufficiency in which the residual capacity is insufficient for causing the endoscope 40 to operate and calculates, on the basis of the battery charging information, a charging completion residual time, which is time until the charging target battery being charged in the charger 20 changes to the completely charged state.

The control section 62 generates a charging current designation signal for controlling the charging current in the power supply section 24 of the charger 20 such that the charging of the charging target battery is completed within the capacity insufficiency residual time, that is, the capacity insufficiency residual time is equal to or longer than the charging completion residual time. Note that the control section 62 performs control of the charging current according to a method same as the method in the first embodiment.

The charging current designation signal from the control section 62 is transmitted to the charger 20 by the 5 GHz band via the radio section 60b. When receiving the charging current designation signal from the processor 60 via the antenna 29, the radio section 21 of the charger 20 gives the charging current designation signal to the control section 22. The control section 22 controls the charging current by the power supply section 24 on the basis of the received charging current designation signal.

Note that the control section 62 stores and manages information concerning the respective batteries on the basis of identification information of the respective batteries in the same manner as in the first embodiment. For example, the control section 22 can transmit the identification information acquired from the respective batteries to the control section 62 via the radio sections 21 and 60b. The control section 62 causes the memory 64 to store the identification information received from the charger 20 and manages information such as the number of times of charging for each of the respective batteries. The control section 62 reads out, from the memory 64, information corresponding to the identification signal from the control section 22 and determines whether the number of times of charging of a battery about to be charged has reached an upper limit. When determining that the number of times of charging has reached the upper limit, the control section 62 issues notification of charging impossibility. The control section 62 transmits the notification to the control section 22 via the radio sections 60b and 21. Consequently, the control section 22 can cause the indicator 28 to display an indication indicating the charging impossibility.

A communication section 67 is also provided in the processor 60. The communication section 67 is controlled by the control section 62 and capable of performing communication with various medical apparatuses. For example, the communication section 67 is configured to be capable of performing communication with the communication section 26 of the charger 20.

Note that the processor 60 is explained as performing all kinds of control concerning the charging. However, it is evident that the control section 22 of the charger 20 may execute a part or the entire control.

Figure 7:
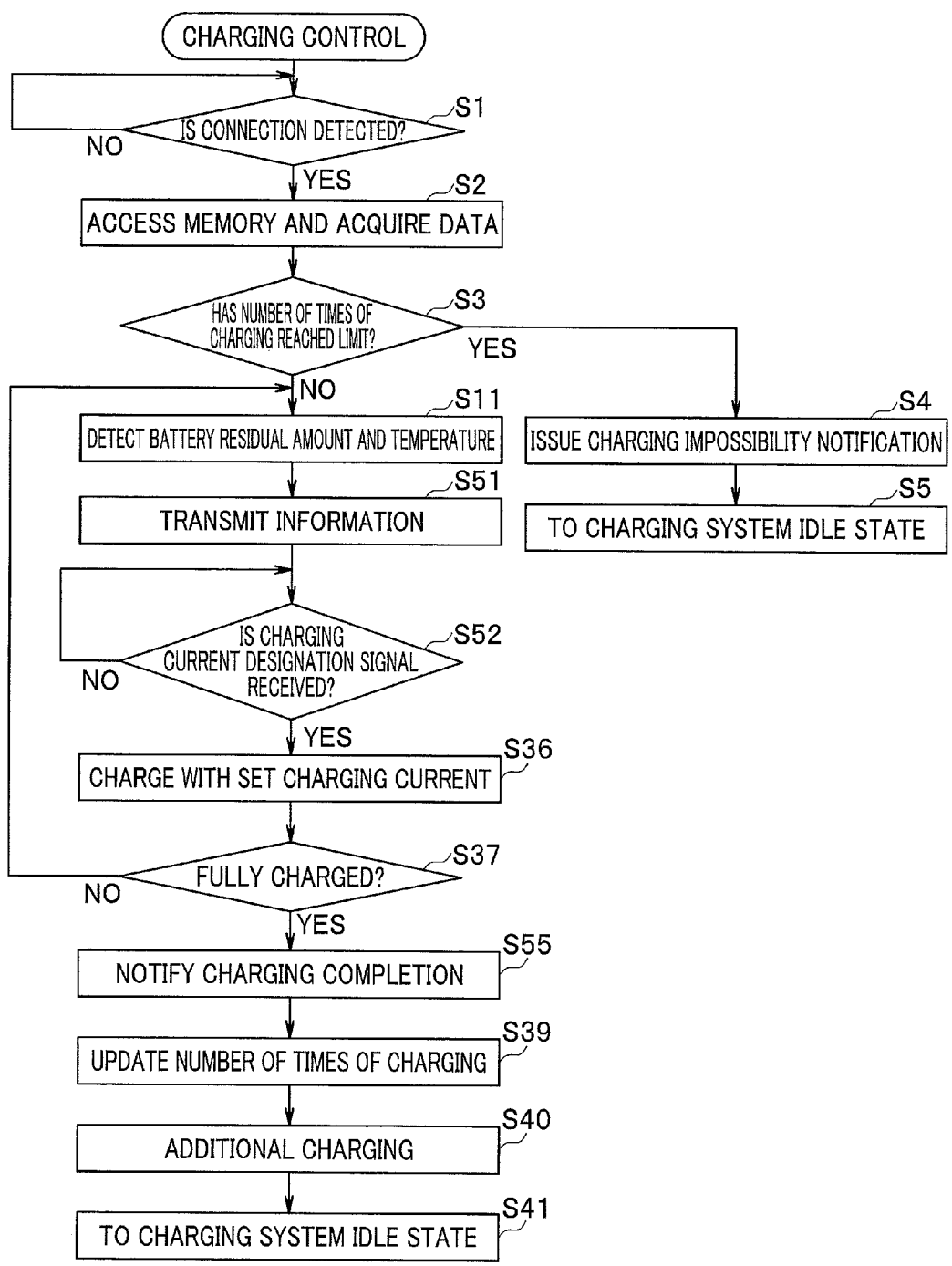
FIG. 7 is a flowchart showing charging control of a control section 22 in the second embodiment.
Figure 8:
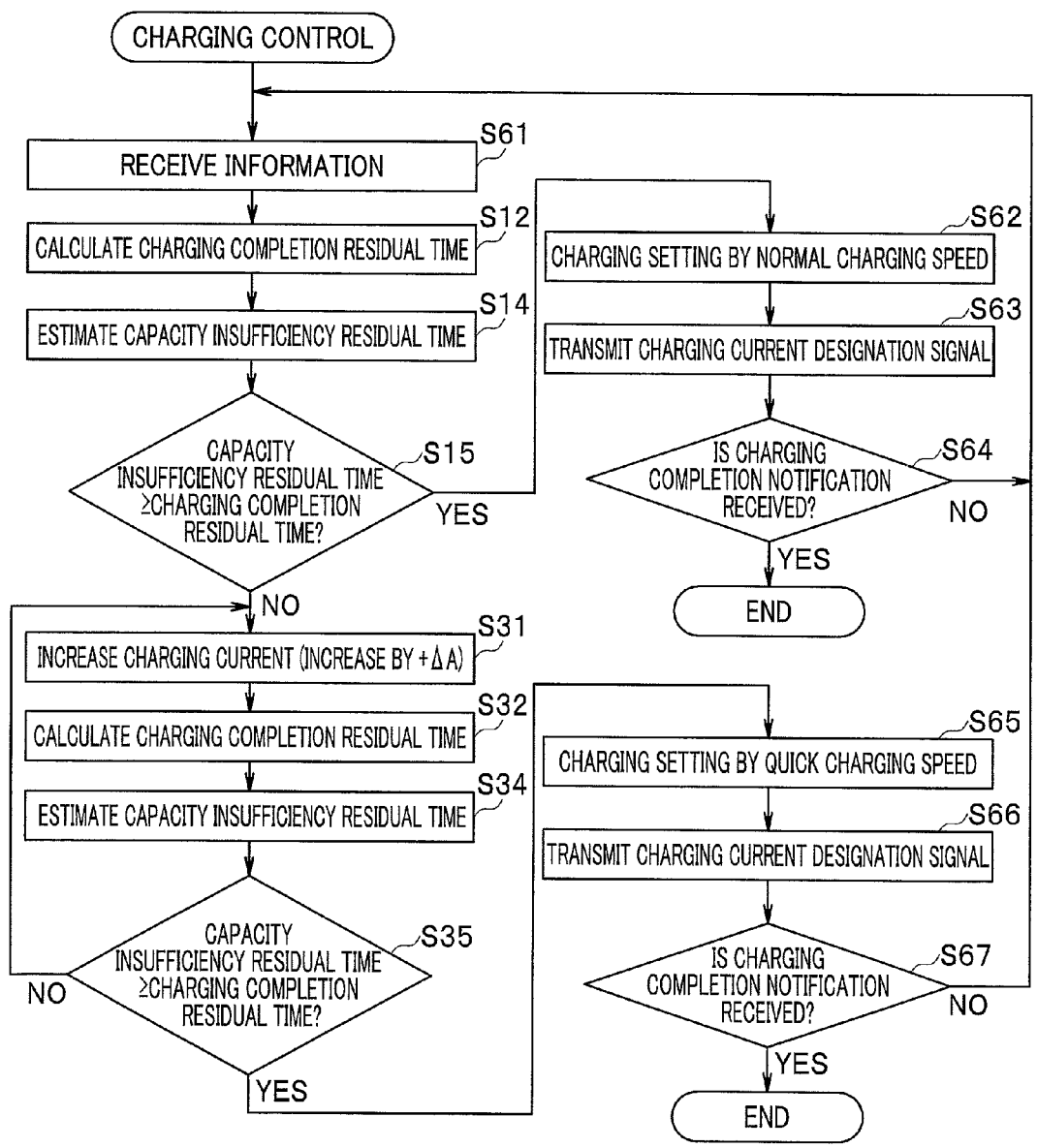
FIG. 8 is a flowchart showing charging control of a control section 62 in the second embodiment.

An operation of the embodiment configured as explained above is explained with reference to FIG. 7 and FIG. 8. FIG. 7 is a flowchart showing charging control of the control section 22 in the second embodiment. FIG. 8 is a flowchart showing charging control of the control section 62 in the second embodiment. In FIG. 7 and FIG. 8, steps same as the steps shown in FIG. 2 are denoted by the same reference signs and explanation of the steps is omitted. An example shown in FIG. 7 and FIG. 8 indicates an example in which the control sections 22 and 62 perform charging control in cooperation with each other.

The charger 20 executes the processing in steps S1 to S5 and S11 in FIG. 7 and acquires battery charging information concerning a rechargeable charging target battery and information concerning an ambient temperature. In step S51, the charger 20 transmits the information concerning the battery charging information and the ambient temperature to the control section 62 of the processor 60 via the radio sections 21 and 60b.

The control section 62 of the processor 60 receives the information in step S61 of FIG. 8. That is, the control section 62 receives the information concerning the battery charging information and the ambient temperature from the charger 20 and receives the battery use information of the battery in use 49 mounted on the endoscope 40.

In steps S12, S14, and S15, the control section 62 determines, on the basis of the received information, whether the charging completion residual time decreases to time equal to or shorter than the capacity insufficiency residual time when the charging target battery is charged with the normal charging current. When determining that the charging completion residual time decreases to the time equal to or shorter than the capacity insufficiency residual time, in step S62, the control section 62 sets the normal charging current. In step S63, the control section 62 transmits a charging current designation signal for charging the charging target battery with the normal charging current.

In step S52, the control section 22 of the charger 20 stands by for reception of the charging current designation signal. When receiving the charging current designation signal from the processor 60, in step S36, the control section 22 sets the charging current designated by the charging current designation signal in the power supply section 24. Consequently, the power supply section 24 performs charging of the charging target battery connected to the battery connecting section 25 with the normal charging current.

In step S37, the control section 22 determines whether the charging is completed. The processing in step S37 is performed at a predetermined time interval. When the charging is not completed, the control section 22 returns the processing to step S11 and acquires information concerning battery charging information and an ambient temperature. These kinds of information are transmitted to the control section 62 of the processor 60 in step S51.

In step S64, the control section 62 determines whether the charging completion notification is received. When the charging completion notification is not received, in step S61, the control section 62 receives the information transmitted by the control section 22 of the charger 20 in step S51 and repeats the processing in steps S12 to S15.

It is assumed that, for example, in step S15, the control section 62 determines that the charging completion residual time exceeds the capacity insufficiency residual time. In this case, in steps S31 to S34 and S35, the control section 62 calculates a charging current with which the charging completion residual time is equal to or shorter than the capacity insufficiency residual time. In step S65, the control section 62 sets the calculated charging current of the quick charging. In step S66, the control section 62 transmits a charging current designation signal for charging the charging target battery with the calculated charging current.

When receiving the charging current designation signal from the processor 60 in step S52, in step S36, the control section 22 of the charger 20 sets the charging current designated by the charging current designation signal in the power supply section 24. Consequently, the power supply section 24 performs charging of the charging target battery connected to the battery connecting section 25 with the charging current of the quick charging. Thereafter, the same operation is repeated. The charging current with which the charging completion residual time is equal to or shorter than the capacity insufficiency residual time is calculated at a predetermined time interval on the basis of the battery use information of the battery in use 49 and the battery charging information of the charging target battery. The charging of the charging target battery is performed with the charging current.

When determining in step S37 that the charging is completed, in step S55, the control section 22 transmits a charging completion notification to the control section 62 of the processor 60. When receiving the charging completion notification in step S64 or S67, the control section 62 ends the processing. The other action is the same as the action in the first embodiment.

Note that the example shown in FIG. 7 and FIG. 8 is an example in which the transmission and the reception of the information are managed on the control section 22 side of the charger 20. However, the transmission and the reception of the information may be managed on the control section 62 side of the processor 60.

As explained above, in the present embodiment, the control section 22 acquires the battery use information of the battery used in the endoscope, acquires the battery charging information of the charging target battery, and updates, on the basis of these kinds of information, at the predetermined time interval, the charging current with which the charging completion residual time is equal to or shorter than the capacity insufficiency residual time. Consequently, irrespective of a state of use of the battery in the endoscope, it is possible to complete the charging of the other batteries before the residual capacity of the battery in use becomes insufficient. It is possible to prevent the charging current from being increasing more than necessary. Therefore, it is possible to continuously use the endoscope while preventing life of the battery from decreasing.

The present invention is not limited to the respective embodiments per se. In an implementation stage, the constituent elements can be modified and embodied in a range not departing from the spirit of the present invention. Various inventions can be formed by appropriate combinations of the plurality of constituent elements disclosed in the respective embodiments. For example, several constituent elements among all the constituent elements described in the embodiments may be deleted. Further, the constituent elements described in different embodiments may be combined as appropriate.

What is claimed is:

1. A medical apparatus system comprising:
a wireless endoscope driven by a first battery, the wireless endoscope having an image pickup device;
a first communication section provided in the wireless endoscope and configured to transmit, by radio, battery use information including information concerning a residual capacity of the first battery;
a charger including a power supply section configured to charge a second battery, which is a charging target;
a second communication section provided in the charger and configured to communicate with the first communication section by radio and acquire the battery use information; and
a control section configured to: (i) cause the second communication section to acquire the battery use information a plurality of times in a period until the second battery changes to a completely charged state, (ii) obtain a capacity insufficiency residual time which is time until the residual capacity of the first battery changes to a state of residual capacity insufficiency based on the battery use information acquired by the second communication section, each time when the battery use information is acquired, and (iii) set a charging current of the power supply section on the basis of the obtained capacity insufficiency residual time and battery charging information including a residual capacity of the second battery included in the charger, such that the capacity insufficiency residual time is equal to or longer than a charging completion residual time, which is time until the second battery changes to the completely charged state.

2. The medical apparatus system according to claim 1, wherein the second communication section acquires the battery use information at a predetermined time interval.

3. The medical apparatus system according to claim 1, wherein the control section sets a minimum current value that is permitted in the charger as the charging current.

4. The medical apparatus system according to claim 1, wherein the control section increases the setting of the charging current stepwise and determines whether the capacity insufficiency residual time is equal to or longer than the charging completion residual time to calculate a charging current to be set.

5. The medical apparatus system according to claim 1, wherein the control section calculates, on the basis of a relation between a charging current and a change in a charging capacity per unit time concerning the second battery, a charging current to be set.

6. The medical apparatus system according to claim 1, wherein the control section causes a memory to store identification information of the second battery and manages a number of times of charging of the second battery.

7. The medical apparatus system according to claim 6, further comprising a code reading section configured to read the identification information of the second battery.

8. The medical apparatus system according to claim 6, wherein, when detecting that the number of times of charging of the second battery reaches an upper limit, the control section issues a charging impossibility notification.

9. A medical apparatus system comprising:
a wireless endoscope driven by a first battery, the wireless endoscope having an image pickup device;
a first communication section provided in the wireless endoscope and configured to transmit, by radio, battery use information including information concerning a residual capacity of the first battery;
a charger including a power supply section configured to charge a second battery, which is a charging target;
a second communication section provided in the charger and configured to transmit battery charging information including a residual capacity of the second battery;
a third communication section configured to communicate with the first communication section and the second communication section and acquire the battery use information and the battery charging information; and
a control section configured to: (i) cause the third communication section to acquire the battery use information a plurality of times in a period until the second battery changes to a completely charged state, (ii) obtain a capacity insufficiency residual time which is time until the residual capacity of the first battery changes to a state of residual capacity insufficiency based on the battery use information acquired by the second communication section, each time when the battery use information is acquired, and (iii) set a charging current of the power supply section on the basis of the obtained capacity insufficiency residual time and the battery charging information acquired by the third communication section, such that the capacity insufficiency residual time is equal to or longer than a charging completion residual time, which is time until the second battery changes to the completely charged state.

10. The medical apparatus system according to claim 9, wherein
the wireless endoscope includes a processor configured to process a picked-up image from the endoscope, and
the third communication section and the control section are provided in the processor.

* * * * *